US005706806A

United States Patent [19]
Kissinger

[11] Patent Number: 5,706,806
[45] Date of Patent: Jan. 13, 1998

[54] LINEAR MICRODIALYSIS PROBE WITH SUPPORT FIBER

[75] Inventor: Candice Brenda Kissinger, West Lafayette, Ind.

[73] Assignee: Bioanalytical Systems, Inc., West Lafayette, Ind.

[21] Appl. No.: 638,642

[22] Filed: Apr. 26, 1996

[51] Int. Cl.$^6$ .................................................. A61B 5/05
[52] U.S. Cl. .................... 128/632; 128/630; 604/27; 604/29
[58] Field of Search ............................ 128/630, 632, 128/633, 635, 637, 760, 768, 769; 604/27, 29, 43, 93, 264, 48; 606/108; 210/650, 500.21, 500.23, 500.28, 500.29

[56] References Cited

U.S. PATENT DOCUMENTS

| | | |
|---|---|---|
| 3,128,769 | 4/1964 | Scuskiwucz . |
| 3,830,106 | 8/1974 | Gardiner et al. . |
| 4,274,417 | 6/1981 | Delpy . |
| 4,340,615 | 7/1982 | Goodwin et al. . |
| 4,694,832 | 9/1987 | Ungerstedt . |
| 4,994,072 | 2/1991 | Bhate et al. . |
| 5,002,054 | 3/1991 | Ash et al. ........................ 128/768 |
| 5,191,900 | 3/1993 | Mishra . |
| 5,449,064 | 9/1995 | Hogan et al. . |
| 5,615,671 | 4/1997 | Schoonen et al. ............... 128/632 |

OTHER PUBLICATIONS

Hong et al., "The Linear Probe: A Flexible Choice for In Vivo Microdialysis Sampling in Soft Tissues"; Current Separations 14:2 (Dec. 1995), pp. 54–57.

*Primary Examiner*—Vincent Millin
*Assistant Examiner*—Robert M. Wieland
*Attorney, Agent, or Firm*—Ice Miller Donadio & Ryan; Doreen J. Gridley

[57] ABSTRACT

An improved linear microdialysis probe assembly has a short semipermeable membrane portion containing a flexible, internal support or reinforcement fiber bonded to long lengths of inlet and outlet robing. Also disclosed is a method of using it to sample the interstitial fluid of a variety of soft tissues in a living animal including dermis, muscle, adipose and subcutaneous tissue, liver and tumors by pulling the fiber, and attached probe, through the tissue of interest with a needle until the membrane is positioned where desired.

9 Claims, 1 Drawing Sheet

LINEAR MICRODIALYSIS PROBE WITH SUPPORT FIBER

FIELD OF THE INVENTION

This present invention relates very generally to surgical devices and more specifically to diagnostic or testing means for collecting liquid within a living body.

BACKGROUND OF THE INVENTION

Biological fluids contained in the extracellular spaces of living tissue, such as in the brain, other organs or subdermal tissue, often must be sampled for research or diagnostic purposes. If ample fluid is available, it may be simply withdrawn and analyzed directly. However, in many instances, only small amounts of fluid are available and sampling must be by indirect methods.

In vivo microdialysis sampling, during which little or no fluid is removed from or introduced into the system, involves implanting a short tubular dialysis membrane at the site of interest then continuously perfusing the interior of the membrane with a solution similar in composition to the body fluid at that site. The dialysate containing chemicals which diffuse through the membrane may easily be collected and analyzed.

For a decade, the use of microdialysis sampling in basic and pharmacokinetics research has proven to have many benefits such as clean samples, more frequent samples, conservation of body fluid, and fewer animals per study. In addition, it provides a direct profile of pharmacokinetics within the tissue of interest instead of traditional methods which calculate the tissue concentration indirectly from serial blood samples. Microdialysis sampling was originally developed for central nervous system ("CNS") studies but during the past several years its suitability for sampling from other sites has been demonstrated.

Various designs of microdialysis probes have been developed for particular sites or types of tissue. For example, the rigid cannula probe (such as the type disclosed in U.S. Pat. No. 4,694,832 by Ungerstedt, for example) is most suitable for sampling from the brain but has also been used to sample from adipose tissue, muscle and liver. It has long been known that such rigid probes often cause tissue damage during insertion and/or use. A flexible cannula probe (such as the type disclosed in U.S. Pat. No. 4,340,615 by Goodwin et at.) has proven more appropriate for sampling from blood, but has also been used in liver. Even though they may have various end geometries, both rigid and flexible cannula probes must have a relatively large overall diameter to accommodate their inlet and outlet tubing since they enter and exit a body at one point. That is, the in and out flowpaths are either looped, side-by-side or concentric as shown in U.S. Pat. No. 5,191,900 by Mishra. Linear design probes (which enter a body at one point, thread through the tissue of interest, and then exit the body at a second point) have been used for pharmacokinetics and metabolism studies of dermal tissue, muscle and tumor, and liver. The linear design has the advantages of minimizing tissue damage (because of its small diameter), being totally flexible (and therefore more comfortable), and usually sufficiently durable for use in awake, freely moving animals. A flow-through or shunt probe has also been designed for use in, for example, the bile duct. However, there are several problems or disadvantages with these prior art devices.

Other dialysis probes or similarly operating sampling devices are disclosed in U.S. Pat. No. 4,274,417 by Delpy; U.S. Pat. No. 3,830,106 by Gardiner et at.; and U.S. Pat. No. 3,128,769 by Scislowicz.

The aforementioned patents are only representative of the art in this area. Nevertheless, despite the large variety of designs and geometries available for sampling probes, there are still problems and a need for improvements in this art. For example, with most such probes, some other device (e.g. a guide cannula, a tunneling needle, or scalpel cut) is required to create a hole or passage into which the probe is placed. Since this hole must be somewhat larger than the outer diameter of the probe, it often causes much tissue damage. In addition, the short length of dialysis membrane required by the prior art designs reduces or slows the amount of sample recovered and makes analysis difficult and/or places constraints on the analytical methodology.

It is therefore an object of the present invention to provide a much smaller and completely flexible dialysis probe and a reliable method of implanting it which would minimize tissue damage to little more than the diameter of the probe itself.

A concern which arises in a probe having a small outer diameter, and hence a small inner diameter, is the recovery characteristics of the probe. Due to the small inner diameter, the velocity of perfusion fluid within the probe at a given volume flow rate is necessarily higher than that of a larger inner diameter probe, thereby reducing the percent relative recovery of the targeted analyte. It is therefore desired to provide a small inner diameter probe which provides the user with some control over the percent relative recovery.

SUMMARY OF THE INVENTION

The present invention aims to overcome some of the disadvantages of the prior art as well as offer certain other advantages by disclosing an improved linear microdialysis probe assembly consisting of a long length of plastic tubing having a short, thin semipermeable membrane window intermediate its ends. The tubing contains a length of strong but flexible, inert reinforcement or support fiber, preferably extending throughout its entire length, but at least extending through the membrane window and out beyond one end of the tubing. The support fiber is attached or bonded to the one end of the tubing to help resist longitudinal stress, thus allowing the probe to have an even smaller cross sectional profile but providing additional strength and flexibility compared to the prior art probes.

The invention also contemplates a method of inserting the new probe in a live animal to sample the interstitial fluid of a variety of soft tissues including dermis, muscle, adipose and subcutaneous tissue, liver and tumors by pulling one end of the fiber, and thus the attached probe, through the tissue with a needle until the membrane window is positioned where desired. The internal support fiber is handled like a suture thread and prevents fracture or over-straining of the thin and fragile membrane during pulling. This method minimizes the tissue damage which would otherwise result from the more common use of an insertion cannula larger than the outer diameter of the new probe. After both ends of the probe are pulled outside the body and secured, the sealed, fiber end is cut off, leaving the fiber inside the probe, and the tubing open. Long lengths of highly flexible plastic tubing may then be connected to the basic probe to convey fluids from the perfusion pump and to the analyzing equipment.

It is possible to implant the membrane portion of the probe in tissues that are quite distant from the exit site for the inlet and outlet tubing. This feature also makes the probe inherently more comfortable for the animal than a probe that must be anchored to skin proximal to the implant site. This new linear probe moves with the tissue and does not jab or tear tissue during normal respiration, digestion, or movement by the animal. As discussed below, this probe was implanted in the thigh muscle of an active flee-moving rat as a test of its ruggedness and stability. Such tests of this probe remained functional for up to six days.

BRIEF DESCRIPTION OF THE DRAWING

While this specification concludes with claims particularly pointing out and the subject matter which is now regarded as the invention, it is believed that the broader aspects of the invention, as well as several of the features and advantages thereof, may be better understood by reference to the following detailed description of a presently preferred embodiment of the invention when taken in connection with the accompanying drawing in which the FIGURE is an illustration of a linear probe for microdialysis constructed according to the teachings of the present invention and showing enlarged views of the membrane window and the insertion end portion of the probe assembly.

DETAILED DESCRIPTION OF THE INVENTION

Figure 1:
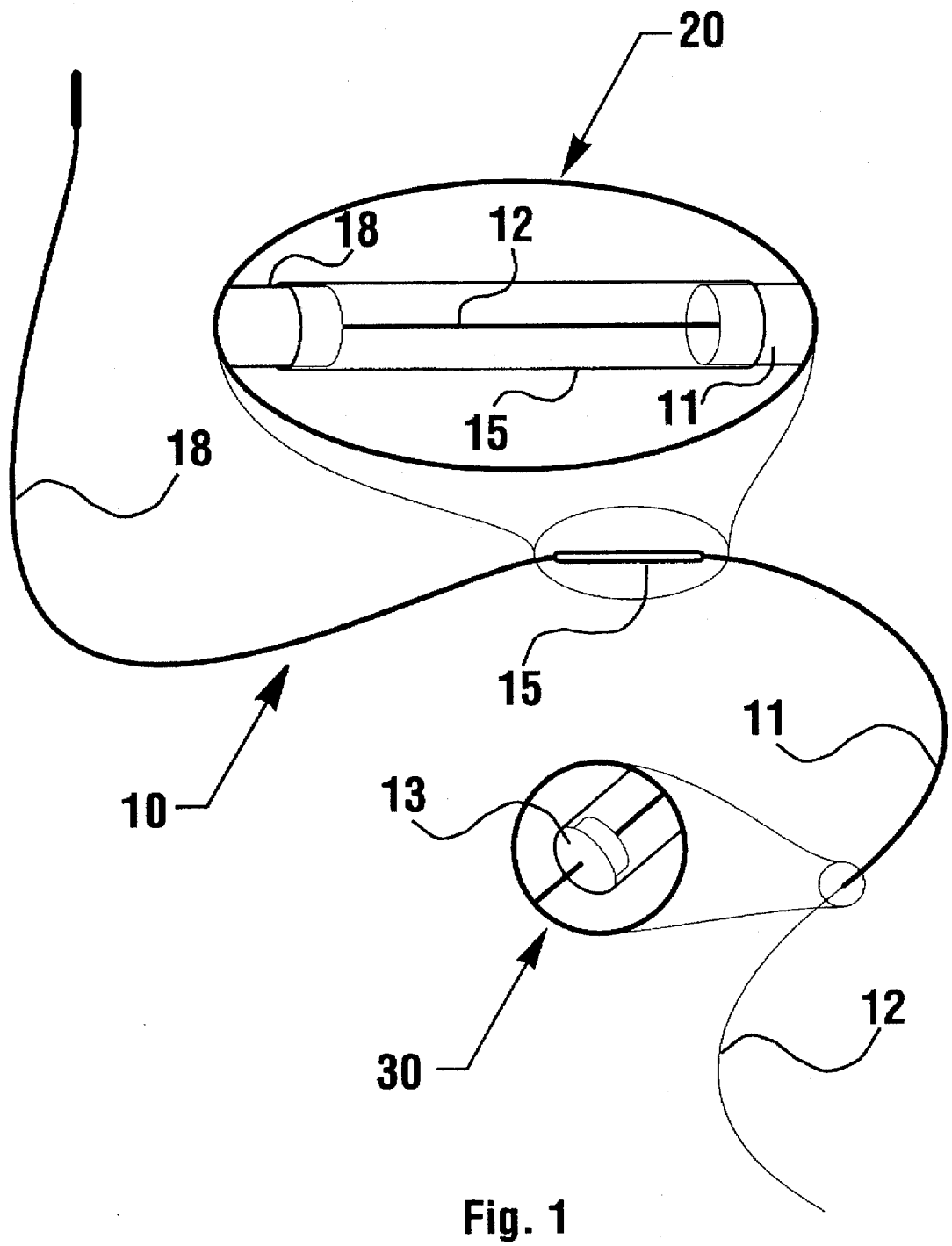

Referring now to the drawings and particularly to the FIGURE, there is shown a preferred embodiment of the present invention in which the probe assembly (10) consists of a short, thin, tubular semi-permeable membrane (15) connected to a length of plastic inlet tubing (11) at one end and to a similar length of outlet tubing (18) at the other end so as to form a window in the probe intermediate its ends. Suitable semipermeable membrane materials are well known in the art and include polyacrylonitrile, cuprophan, regenerated cellulose, polycarbonate, polysulfone and the like. Since the membrane (15) is relatively weak and fragile compared to the plastic tubing (11, 18), a reinforcement or support fiber (12) extends through the membrane (15) and out the inlet tubing (11) where an end plug or seal (13) secures it as part of the probe assembly (10). Suitable support fiber materials include stainless steel, polymethyl methacrylate, polybutylene terephthalate, glass and similar biocompatible monofilaments.

During use, the probe (10) is surgically inserted, usually by pulling with a large needle (hence the need for strength), into a live animal (or person) where the extracellular biological fluid within the tissue of interest may be sampled through the semi-permeable membrane (15). The seal (13) prevents contamination of the inside of the probe tubing (11, 18) by body fluids during surgical insertion as well as providing the anchor point for the support fiber (12). To sample such biological fluid, a perfusion solution (i.e. an inert carrier such as saline solution) is pumped (by any common pump means such as a syringe, not shown) through the inside of the inlet tubing (11) to the membrane (15) where various low molecular weight chemical compounds in the tissue fluid adjacent the outside of the probe migrate across or diffuse through the membrane (15) into the solution to form an analyte which continues to flow via the outlet tubing (18) until it exits the probe (10). This probe effluent, containing the chemical compounds of interest carded in the perfusion solution, can then be analyzed by any of the well known methods, such as immuno-assay, chromatography or electrophoresis. One suitable electrophoresis system and method of using it with a microdialysis probe is disclosed in U.S. Pat. No. 5,449,064 which is incorporated herein by reference. Practical uses of the present invention are discussed in more detail below.

Pharmacokinetics Experiments:

Male Sprague-Dawley rats weighing 450–480 grams each were anesthetized intramuscularly using ketamine and xylazine (80 mg/kg and 10 mg/kg, respectively). An incision was made in the skin to expose the thigh muscle. A linear probe (10) was constructed according to the present invention with a cross section of about 180 µm and an overall length of about 51 cm. It was implanted in the muscle tissue of the thigh by inserting a 25 gauge needle through the muscle and inserting one end of the probe inlet tubing (11) through the needle's eye. The needle was then withdrawn and the probe (10) pulled through the tissue, placing the 10 mm length of dialysis membrane (15) fully inside the muscle. The internal support fiber (12) prevented fracture or over-straining the fragile membrane (15) during pulling. Once the probe (10) is implanted, the user has the option of removing the support fiber (12) to increase the flow area within the probe (10) and thus decrease the flow rate at the same pump settings which, in turn, increases the percent relative recovery. Such removal of the support fiber (12) requires detachment of the support fiber (12) from the inlet tubing (11) and removal of the support fiber (12) from within the membrane (15) or from within both the membrane (15) and the tubing (11, 18) by pulling the support fiber (12) at its end proximate the seal (13). Retention or reinsertion of the support fiber (12) into the tubing (11, 18) so that the support fiber (12) once again resides within the membrane (15) results in a decrease in the percent relative recovery of the probe (10) under constant pump flow rate conditions by decreasing the flow area within the probe (10), and, more specifically, by decreasing the flow area of the membrane (15), which increases flow velocity inside the membrane (15).

A length of PE 50 plastic tubing was cannulated into the femoral vein of the other leg for administration of drugs. The probe tubing (11, 18) and the cannula were tunneled under the skin and externalized at the center of the back of the neck. Following this surgical procedure, the rat was maintained in an awake animal system, which allowed movement without tangling of fluid lines. The rat had free access to food and water throughout the experiment.

An in vitro probe calibration procedure was used to relate percent recovery to percent delivery. Recovery was determined by using Ringer's solution spiked with a known concentration of acetaminophen. Delivery was determined by perfusing the probe (10) with a solution having a known concentration of acetaminophen and then monitoring the decrease in concentration in the probe effluent. Recovery and delivery in vitro were conducted in stirred solutions maintained at 37° C. At the beginning of each experiment, the probe was perfused for 30 minutes prior to collecting five dialysate samples at 10 minute intervals. In vitro recovery and delivery were then calculated as follows:

$$\text{Recovery \%} = C_d/C_i \times 100\%$$

$$\text{Delivery \%} = 1 - C_d/C_i \times 100\%$$

where $C_d$ is the concentration of a given compound in the dialysate and $C_i$ is the concentration of the same compound in the initial standard solution. Since recovery and delivery are derived values, the standard deviations were calculated by propagation of errors. An in vivo delivery calibration procedure was performed in a similar manner as the in vitro experiment, except that the probe was implanted in the muscle as described above. The initial delivery experiment began 3 to 4 hours after surgery (day 0) and was repeated daily.

On days 1 and 5, pharmacokinetics experiments were performed by perfusing the implanted probe with Ringer's solution at 2 µL/min. Samples were continuously collected over 10 minute intervals. Two blank samples were collected prior to dosing and no interferences were observed in these samples. A dose of acetaminophen (25 mg/kg) in 1 mL saline solution was administered into the femoral vein. Dialysate samples were collected for 4 hours after dosing at 10 minute intervals. Concentrations of acetaminophen were calculated by determining the dialysate concentration from a standard curve and corrected by using the in vivo delivery calibration data for the dialysis probe. Data acquisition and Pharmacokinetics Analysis (PKA) software from the assignee of this invention was used to convert the original chromatographic dam (obtained from a BAS 200 liquid chromatograph with internal UV detector settings of 250 nm) to concentrations and then plot and fit the pharmacokinetics data curves.

shown that acute inflammatory response of the tissue to the implantation and indwelling of the probe can affect its behavior.

The foregoing experiments illustrate the utility of microdialysis sampling in peripheral tissues for studying the disposition of a drug in vivo. In particular the reliability and durability of the new linear probe were demonstrated. While absolute calibration of the microdialysis probe is very difficult in tissue, normalization procedures can be used for experiment-to-experiment and time-to-time comparisons.

It will be appreciated by those of skill in the art that the probe of the present invention is smaller than those of the prior art while maintaining complete flexibility to enable the probe to be used without causing significant tissue damage during insertion and without causing damage to tissue when implanted within the animal. Thus, the animal is free to move after probe implantation.

TABLE 1

| Probe No. | Recovery % | Delivery % | Day 0 | Day 1 | Day 2 | Day 3 | Day 4 | Day 5 |
|---|---|---|---|---|---|---|---|---|
| 1 | 33.9 ± 0.1 |  | 48 ± 1 | 34 ± 1 | 24.7 ± 0.5 | 26 ± 4 |  |  |
| 2 | 43 ± 2 | 47.2 ± 0.2 | 43.6 ± 0.3 | 31 ± 1 |  |  | 29 ± 2 | 31.7 ± 0.5 |
| 3 | 63 ± 2 | 66.8 ± 0.5 | 30 ± 3 | 46 ± 2 | 37 ± 1 | 30.5 ± 0.2 | 27 ± 3 | 27 ± 6 |
| 4 | 63.1 ± 0.2 | 60.5 ± 0.3 |  |  |  |  |  |  |
| in: | vitro | vitro | vivo | vivo | vivo | vivo | vivo | vivo |

In vitro recoveries and deliveries are shown in the left hand columns of Table 1. None of the probes showed a significant difference between recovery and delivery in vitro. Theoretically, in a stirred solution around the probe at constant temperature and perfusion flow rate, recovery and delivery of a given compound should be the same. Our results supported this theory and are in agreement with previously reported findings. We used the agreement of recovery and delivery in Vitro as an initial evaluation of the reliability of the probe. Table 1 also includes, in the right hand columns, the daily averages for delivery in vivo. These were lower than in vitro deliveries for the same probe. That in vivo delivery is different from in vitro delivery is not unexpected, since it is well known that in vivo recovery and delivery depends mainly on the properties of the medium surrounding the probe. Several approaches have been used to determine in vivo recovery. In vivo delivery of the analyte of interest has also been validated as a means of determining in vivo recovery in muscle. Using in vivo delivery to correct the dialysate concentrations is more accurate than using in vitro recovery. Our results showed that in vivo deliveries changed from day to day in the same animal. Therefore, the daily in vivo delivery value appears to be a better parameter for calculating the actual concentration of analyte in the tissue interstitial fluid. No interferences were observed in the samples obtained prior to dosing. Typical concentration-time profiles of acetaminophen in the muscle of another rat on days 1 and 5 showed that the $t_{1/2}$ of the absorption phase was 16 minutes for day 1 and 29 minutes for day 5 of the experiment. The $t_{1/2}$ of the elimination phase was 37 minutes for day 1 and 46 minutes for day 5 of that experiment. The peak concentration of acetaminophen in muscle dialysate was about 25 µM on day 1 and about 19 µM on day 5. The difference between in vivo delivery on days 1 and 5 of these experiments might be due to a change in circulation or diffusion in the tissue surrounding the probe under different circumstances (time of recovery after surgery, activity of the animal, or similar considerations). Other researchers have It will also be appreciated that the probe of the present invention may be implanted in tissues that are distant from the exit sites for the inlet and outlet tubing. This feature is advantageous when compared to probes which must be anchored to skin proximate to the implant site. Greater flexibility is provided to the user for placement of the inlet and outlet tubing, and the probe may be implanted in a more comfortable position for the animal.

It will be further appreciated that the probe of the present invention provides a mechanism to allow the user to control the percent relative recovery of the targeted analyte. It is well known in the art that decreasing the flow rate of perfusion fluid within the probe thereby increases the percent relative recovery by reducing the concentration gradient between the perfusion fluid and the sample. Such control is not practicable in all instances, however, such as when using a perfusion pump already operating at a very low flow rate. The probe of the present invention provides the user with another method to increase percent relative recovery by removal of the reinforcement or support fiber (12). Keeping the flow at the perfusion pump constant, removal of support fiber (12) decreases the flow rate of perfusion within the probe and thereby increases the percent relative recovery of the targeted analyte. Re-insertion of the support fiber (12) into the probe results in a reduction in percent relative recovery of the targeted analyte and may be desired under certain circumstances. Use of a removably attached support fiber with the tubing of the probe may be used in conjunction with prior art probes, whether flexible or not, to provide control of the percent relative recovery of the probe.

While the present invention has been described in terms more or less specific to one preferred embodiment, it is expected that various alterations, modifications, or permutations thereof will be readily apparent to those skilled in the art. Therefore, it should be understood that the invention is not to be limited to the specific features shown or described, but it is intended that all equivalents be embraced within the spirit and scope of the invention as defined by the appended claims.

It will be appreciated that the use of an internal fiber attached to one end of the probe tubing provides protection for the interior of the probe during insertion into tissues, a tool for probe insertion which minimizes tissue damages, and a means of protecting the probe membrane against fracture or over-straining during insertion. Furthermore, the internal fiber supports the probe by resisting bending or crimping of the soft probe membrane while it is inside an active, moving animal so that flow can be maintained.

What is claimed is:

1. An improved linear microdialysis probe assembly, adapted for sampling the interstitial fluid of a variety of soft tissues in living animals, comprising: a length of plastic tubing having a tubular semipermeable membrane window intermediate its ends, and a length of flexible support fiber positioned within and attached to the tubing and extending at least through the tubular membrane window.

2. The probe assembly of claim 1 wherein the semipermeable membrane is selected from the group of materials consisting of polyacrylonitrile, cuprophan, regenerated cellulose, polycarbonate, polysulfone and the like.

3. The probe of claim 1 wherein the support fiber is selected from the group of materials consisting of stainless steel, polymethyl methacrylate, polybutylene terephthalate, glass and similar biocompatible monofilaments.

4. The probe of claim 1, wherein the support fiber is removably attached to the tubing such that the support fiber may be removed from within the robing and the window.

5. A method of inserting a microdialysis probe, of the type having a length of plastic tubing having a tubular semipermeable membrane window intermediate its ends and a length of flexible support fiber positioned within and attached to the tubing and extending at least through the tubular membrane window, into a live animal to sample the interstitial fluid of soft tissues therein, the method comprising the step of: pulling one end of the fiber, and thus the attached probe, through the tissue with a needle until the membrane window is positioned where desired.

6. The method of claim 5, wherein the support fiber is removably attached to the tubing, the method further comprising the steps of: detaching the support fiber from the tubing, and pulling the support fiber so that it no longer is positioned within the tubing.

7. A microdialysis probe assembly, comprising: a semipermeable hollow membrane, hollow tubing connected to the membrane, and a support fiber removably attached to the tubing and positioned within the tubing and the membrane when attached to the tubing.

8. A method of controlling the percent relative recovery of a microdialysis probe comprising a hollow membrane, hollow tubing connected to the membrane, and a support fiber removably attached to the tubing and positioned within the tubing and membrane when attached to the tubing, the method comprising the steps of: implanting the probe having the support fiber attached to the tubing, detaching the fiber from the tubing, and removing the fiber from the probe so that it no longer resides within the membrane, to thereby increase the percent relative recovery of the probe in the presence of a constant flow rate of a perfusion promp connected to the tubing.

9. The method of claim 8, further comprising the steps of: re-inserting the fiber into the membrane to thereby decrease the percent relative recovery of the probe.

* * * * *